United States Patent [19]

Stewart et al.

[11] 4,254,023

[45] Mar. 3, 1981

[54] SYNTHESIS OF PEPTIDE ALCOHOLS BY THE SOLID PHASE METHOD

[75] Inventors: John M Stewart, Denver; Dan H. Morris, Broomfield, both of Colo.

[73] Assignee: Pennwalt Corporation, Philadelphia, Pa.

[21] Appl. No.: 85,231

[22] Filed: Oct. 16, 1979

[51] Int. Cl.³ .......................................... C07C 103/52
[52] U.S. Cl. ............................................ 260/112.5 R
[58] Field of Search ................... 260/112.5 R; 424/177

[56] References Cited

PUBLICATIONS

Sorrell, et al., Tetrahedron Letters No. 28, pp. 2473-2474 (1978).
Kikergawa, Chem. Abstr., vol. 91 (1979), 38304u.

Primary Examiner—Delbert R. Phillips
Attorney, Agent, or Firm—Allan R. Plumley; John S. Roberts, Jr.

[57] ABSTRACT

A method for preparing novel peptide alcohols exemplified by the reduction of enkephalins and particularly the met-enkephalin to produce pentapeptides and tetrapeptides of the following formula H-Tyr-DAla-Gly-Phe-Methioninol (1)

H-Tyr-DAla-Phe-Methioninol (2)

Additional alcohols having a carbon or C-number exceeding or less than 4 or 5 may also be prepared. These compounds are produced by solid phase peptide synthesis developed by R. B. Merrifield in *Advances in Enzymology*, 32:221 (1969) in which the terminal carboxyl group is reduced to the alcohol under the influence of lithium borohydride.

7 Claims, No Drawings

SYNTHESIS OF PEPTIDE ALCOHOLS BY THE SOLID PHASE METHOD

BRIEF SUMMARY OF THE INVENTION

Certain pentapeptides are known and it is believed originated with John Hughes of Aberdeen, Scotland. These compositions are analgesics and are as follows:

H-Tyr-Gly-Gly-Phe-Met-OH (Hughes met enkephalin)

H-Tyr-Gly-Gly-Phe-Leu-OH (Hughes leu enkephalin)

The methods of the present invention are exemplified by the preparation of the compositions:

H-Try-DAla-Gly-Phe-Met-alcohol (See Example 1)

H-Tyr-DAla-Phe-Met-alcohol (See Example 2)

Pyroglu-D-Phe-Trp-Ser-Tyr-D-Trp-Leu-Arg-Pro-A-Alaninol (See Example 3)

of which the compositions of Examples 1 and 2 also have been found to be extremely potent analgesics.

The present invention relates to methods in which the carboxy terminal group of low molecular weight peptide is reduced to an alcohol under solid phase conditions. These materials have been synthesized exclusively by the solution method of synthesis in the prior art. Solid phase peptide synthesis affords great advantages in saving time in the synthesis of peptides but heretofore it has not been possible to synthesize peptide alcohols by this method. The method generally is known as the Merrifield method which has been described in an article by R.B. Merrifield entitled "Solid Phase Peptide Synthesis," *Advances in Enzymology*, 32:221–296 (1969).

DETAILED DESCRIPTION OF THE INVENTION

The present peptides which include tetrapeptides and pentapeptides differ in structure from the enkephalins above and it has been found that the present compounds are analgesics which are highly active by intravenous or subcutaneous injection and are even active by oral administration. The ability to synthesize the present compounds by the solid phase method opens a method for synthesis of an important class of peptides and it can be applied to the preparation of a variety of peptides with a terminal alcohol group.

In the solid phase method of peptide synthesis, peptides are synthesized with the peptide chain attached to an insoluble polystyrene resin bead. Peptides can be cleaved from the beads to give the finished product by several different methods, although cleavage to yield a peptide alcohol has not been previously described. Therefore, this is a unique and new application of the solid phase method of peptide synthesis. It is believed that the present application, which involves lithium borohydride as a treating agent in the reduction of peptide esters in the production of peptide alcohols, is new. It is noted that alkali metal borohydride incorporating sodium or potassium may be substituted for lithium borohydride as the reducing agent.

Process Parameters

In the examples below and in the general description of the present invention, a moderate excess of lithium borohydride may be utilized and the reaction carried out at room temperature for a time period of 1–2 hours. Using these parameters, excellent yields of pure products have been obtained. As process alternatives for manufacturing the pentapeptide or tetrapeptide, LiBH$_4$ may be pre-dissolved in tetrahydrofuran (THF) before adding to the resin. Additionally, as to variation in time, the reaction may be allowed to proceed for about 1 hour longer than the time period noted—in other words, a total reaction time of 2–3 hours.

EXAMPLE 1

Synthesis of H-Tyr-DAla-Gly-Phe-Methioninol

Synthesis of the peptide-resin,

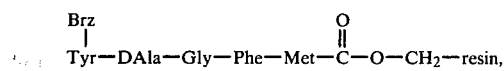

was performed in the standard way on a Beckman 990 synthesizer using 1% crosslinked Merrifield resin (Lab Systems). 800 mg of the dried peptide-resin was suspended with stirring in 30 ml tetrahydrofuran (previously distilled over LiAlH$_4$ to remove peroxides) in a 100 ml round-bottom flask. Then 53 mg LiBH$_4$ (ALFA) was introduced slowly (approximately 10-fold molar excess over Met-substituted resin value, or 5-fold molar excess over ester links taking into account BrZ protecting group or Tyr) with mixing to form a milky suspension. The reaction mixture was stirred 50 min. at room temperature, after which 1 ml glacial HOAc was added to destroy excess LiBH$_4$. The mixture was filtered through a sintered glass funnel and the resin was washed several times with HOAc. Solvents were evaporated under reduced pressure and the residue was lyophilized from glacial HOAc. Approximately 353 mg of product (crude peptide+ Li salts)was obtained; it showed positive ninhydrin and Pauly reactions. The peptide was purified by countercurrent distribution using n-butanol:acetic acid: water (nBAW) 4:1:5, 100 transfers (k=1.94). 56.3 mg of pure peptide (Tyr-DAla-Gly-Phe-Met-ol, single spot on TLC and HVE, Nin+, Pauly+, amino acid ratios correct with no detectable Met) was recovered.

For comparison, 715 mg of the same peptide-resin was subjected to cleavage by HF in the usual fashion (0° C., 45 min. in presence of anisole). 153 mg of crude peptide was recovered and countercurrented under the same conditions as above. The main CCD peak (k=2.03) yielded 56.8 mg of Tyr-DAla-Gly-Phe-Met-COOH.

Under these conditions of reductive cleavage, the yield of pure peptide alcohol was comparable to the yield of the free peptide acid after HF. No effort has yet been made to find optimum reaction conditions. The bromocarbobenzoxy group was removed from tyrosine simultaneously by the reduction.

This reaction will also cause reduction of Asp and Glu side-chain carboxyls if they are present as esters. This could be avoided by using phenacyl esters of these amino acids and removing the esters of thiolysis prior to the LBH reduction.

EXAMPLE 2

Synthesis of H-Tyr-DAla-Phe-Methioninol

Solid phase peptide synthesis of the tetrapeptide-alcohol, Tyr-DAla-Phe-Met-ol, was performed essentially in the same manner as described for the pentapeptide Tyr-DAla-Gly-Phe-Met-ol. In the tetrapeptide synthesis, 2 g of the peptide resin, Tyr(BrZ)-DAla-Phe-Met-OCH$_2$-resin (1% cross-linked Merrifield resin), was placed into a 100 ml round-bottomed flask. Then, 133 mg LiBH$_4$ (ALFA) (about 10 equiv. excess over resin substitution value for Met) dissolved in 75 ml tetrahydrofuran (THF, peroxide-free) was added. A drying tube was placed on the flask and the reaction mixture stirred at room temperature for 2 hours. Excess LiBH$_4$ was destroyed with glacial HOAc and the mixture then filtered through a coarse sintered-glass funnel. After several washes of the resin with glacial HOAc, the solvents were evaporated under reduced pressure and freeze-dried. The crude lyophilized peptide (Pauly+) and remaining Li salts were then subjected to countercurrent distribution in nBAW, 4:1:5, for 100 transfers. CCD cuts were made to maximize purity rather than yield. Some 355 mg peptide was recovered from the various cuts and all cuts contained the major product in excess over any impurities. A particularly homogeneous cut, N-132(67-75), k=2.70, yielded 55 mg of essentially pure peptide, Tyr-DAla-Phe-Met-ol. (TLC: nBAW 12:3:5, silica gel, R$_f$=0.70, Nin+, Pauly+, HVE: 1M HOAc, pH 2.8, 60 min. at 1 KV, E$_{lys}$=0.44, Nin+, Pauly+; amino acid analysis: Tyr (0.99), (D)Ala(1.01), Phe(1.01), Met(0.0), Met-ol was not detectable on analyzer.)

EXAMPLE 3

Synthesis of Pyroglu-D-Phe-Trp-Ser-Tyr-D-Trp-Leu-Arg-Pro-D-Alaninol

This peptide alcohol was synthesized in a manner analogous to that utilized in Example 1 above. The peptide was recovered in good yield. TLC: nBAW 12:3:5, silica gel, Rf=0.59, n BAWP 15:3:12:10, silica gel, Rf=0.67. Amino acid analysis: Trp (1.52), Arg (1.00), Ser (0.95), Glu (0.89), Pro (1.10), Leu (0.99), Tyr (1.07), Phe (0.99). The alanine residue was confirmed by cleaving an aliquot of the same peptide resin by HF and analyzing for alanine in the usual manner.

We claim:

1. A method of synthesizing a peptide alcohol represented by one member of the group consisting of low molecular weight peptides produced from a peptide of similar number of amino acids which comprises reducing the terminal carboxyl group in the presence of a moderate excess of alkali metal borohydride under solid phase conditions at room temperature for about 1–3 hours and recovering a cleaved product containing the peptide product.

2. The method of claim 1 wherein the peptide starting material is a tetrapeptide.

3. The method of claim 1 wherein the peptide starting material is a pentapeptide.

4. The method of claim 1 wherein the reducing agent is lithium borohydride.

5. The method of claim 1 wherein there is utilized as a solvent tetrahydrofuran peroxide free and wherein the excess lithium borohydride is destroyed by glacial acetic acid.

6. The method of claim 1 wherein the synthesis of Tyr-DAla-Gly-Phe-Met-alcohol is produced from

7. The method of claim 1 wherein the synthesis of Tyr-DAla-Phe-Met-alcohol is produced from

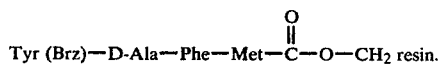

* * * * *